US008735059B2

(12) United States Patent
Song et al.

(10) Patent No.: US 8,735,059 B2
(45) Date of Patent: May 27, 2014

(54) METHODS FOR DETERMINATION OF HAPLOTYPE DISSECTION

(75) Inventors: Qing Song, Decatur, GA (US); Li Ma, Atlanta, GA (US); Yan Xiao, Norcross, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

(21) Appl. No.: 13/267,409

(22) Filed: Oct. 6, 2011

(65) Prior Publication Data

US 2012/0208183 A1 Aug. 16, 2012

Related U.S. Application Data

(63) Continuation of application No. 12/457,697, filed on Jun. 18, 2009.

(60) Provisional application No. 61/136,992, filed on Oct. 21, 2008.

(51) Int. Cl.
C12Q 1/68 (2006.01)

(52) U.S. Cl.
USPC .......................................... 435/6.1

(58) Field of Classification Search
USPC ............................... 435/91.2, 810
See application file for complete search history.

(56) References Cited

U.S. PATENT DOCUMENTS

| 6,850,846 B2* | 2/2005 | Wang et al. .............. 702/19 |
| 2003/0027150 A1 | 2/2003 | Katz |
| 2003/0059808 A1 | 3/2003 | Liu et al. |
| 2004/0224331 A1 | 11/2004 | Cantor et al. |
| 2005/0181394 A1* | 8/2005 | Steemers et al. ........... 435/6 |
| 2005/0233321 A1* | 10/2005 | Hess et al. ................ 435/6 |
| 2008/0228457 A1* | 9/2008 | Mishra et al. .............. 703/11 |

FOREIGN PATENT DOCUMENTS

| WO | 2007/062486 A1 | 6/2007 |
| WO | 2008/148161 A1 | 12/2008 |

OTHER PUBLICATIONS

Li et al., Bioinformatics, vol. 212, No. 24, pp. 4384-4393, 2005.*
Extended European Search Report, issued Sep. 27, 2012 (Application No. EP 09820934.9, International Filing Date Jun. 18, 2009).
Geigl, J.B., et al., "Single-cell isolation from cell suspensions and whole genome amplification from single cells to provide templates for CGH analysis", Nat. Protoc., vol. 2, No. 12, pp. 3173-3184 (2007).
Kroneis, T., et al., "Combined molecular genetic and cytogenetic analysis from single cells after isothermal whole-genome amplification", Clin. Chem., vol. 57, No. 7, pp. 1032-1041 (2011).
Ma, L., et al., "Direct determination of molecular haplotypes by chromosome microdissection", Nature Methods, vol. 7, No. 4, pp. 299-301 (2010).
Nowak, N. J., et al., "Challenges in array comparative genomic hybridization for the analysis of cancer samples", Genet. Med., vol. 9, No. 9, pp. 585-595 (2007).
Konfortov, B.A., et al., "An efficient method for multi-locus molecular haplotyping", Nucleic. Acids. Res., vol. 35, No. 1, pp. e6 (2007).
Burgtorf, et al., Clone-based systematic haplotyping (CSH): a procedure for physical haplotyping of whole genomes, Genome Research, Cold Spring Harbor Laboratory Press, 2003, pp. 2717-2724.
Ding, et al., Direct molecular haplotyping of long-range genomic DNA with M1-PCR, Applied Biological Sciences, PNAS, vol. 100, No. 13 pp. 7449-7453, Jun. 2003.
Di Martino. et al., Single Sperm cell isolation by laser microdissection, Forsenic Science International, Elsevier Ireland Ltd., 2004, pp. S151-S153.
Douglas, et al., Experimentally-deprived haplotypes substantially increase the efficiency of linkage disequilibrium studies, Nature Genetics,Nature Publishing Group, vol. 28, 2001, pp. 361-364.
Hodge, Loss of information due to ambiguous haplotyping of SNPs, Nature Genetics, Nature America Inc., vol. 21, 1999, pp. 360-361.
Li, et al., Amplification and analysis of DNA sequences in single human sperm and diploid cells, Nature, vol. 335,1988 pp. 414-417.
Liu, et al., Haplotype-Association Analysis, Advances in Genetics, Elsevier Inc., vol. 60, 2008.
Michalatos-Beloin, et al., Molecular haplotyping of genetic markers 10kb apart by allele-specific long-range PCR, Nucleic Acids Research, Oxford University Press, vol. 24, 1996, pp. 4841-4843.
Yu, et al., ADLAPH: A molecular haplotyping method based on allele-discriminating long-range PCR, Genomics, Elsevier Inc., vol. 84, 2004, pp. 600-612.
Zhang, et al., Long-range polony haplotyping of individual human chromosome molecules, Nature Genetics, Nature Publishing Group, vol. 38, No. 3, 2006, pp. 382-387.
Nagy, et al., Haplotype-specific extraction: a universal method to resolve ambiguous genotypes and detect new alleles—demonstrated on HLA-B, Tissue Antigens, The Authors Journal compilation, vol. 60, 2007, pp. 176-180.
Mitra, Digital genotyping and haplotyping with the polymerase colonies, PNAS, 2003, vol. 100, pp. 5926-5930.
International Search Report (Application No. PCT/US2009/047765, filed Jun. 18, 2009).
International Preliminary Report on Patentability (Application No. PCT/US2009/047765, filed Jun. 18, 2009).

* cited by examiner

*Primary Examiner* — Cynthia B Wilder
(74) *Attorney, Agent, or Firm* — Ping Wang; Andrews Kurth LLP

(57) ABSTRACT

A method for molecular haplotyping of a subject is disclosed. The method comprises: randomly selecting a set of chromosomes in each of a plurality of lyzed diploid cells of the subject, collecting the selected chromosomes from said plurality of cells into a plurality of sample tubes, wherein each sample tube contains chromosomes selected from one or more cells, genotyping genomic DNA in each sample tube, and determining haplotype of the alleles based on allele nucleotide sequence information and corresponding nucleotide signal intensities from genotyping data. Other methods for molecular haplotyping using single cell lysate or single cell microdissection are also disclosed.

7 Claims, 8 Drawing Sheets
(5 of 8 Drawing Sheet(s) Filed in Color)

METHODS FOR DETERMINATION OF HAPLOTYPE DISSECTION

RELATED APPLICATIONS

This application is a continuation application of the U.S. patent application Ser. No. 12/457,697, filed Jun. 18, 2009, which claims priority from U.S. Provisional Application Ser. No. 61/136,992, filed Oct. 21, 2008. The entirety of all of the aforementioned applications is incorporated herein by reference.

FIELD

The present invention generally relates to the fields of genetics, molecular and cell biology and, in particular, relates to methods for haplotype determination.

BACKGROUND

Normal human somatic cells are diploid (i.e., having two copies of genome: a paternal set of chromosomes and a maternal set of chromosomes in each nucleus). Within each individual, these two sets of chromosomes have different nucleotide sequences (single-nucleotide polymorphism (SNP)) at multiple loci. Conventional genotyping assays analyze a mixture of these two sets of chromosomes, which leads to uncertainty and complexity. For example, for any two SNP loci that are both heterozygous, there will be four possible haplotypes between these two SNPs. However, since the phase information was erased when doing the single SNP genotyping using the conventional platforms, none of these four possible haplotypes can be eliminated. One way to solve this problem is to find a reliable method to re-establish or retract the phase information. Another way is to extract the phase information before doing genotyping.

The skilled artisans in this field used the various statistical algorithms to re-establish the phase information. These algorithms include Clark's algorithm, expectation-maximization (EM) algorithm, coalescence-based algorithms (pseudo-Gibbs sampler and perfect/imperfect phylogeny), and partition-ligation algorithms implemented by a fully Bayesian model (Haplotype) or by EM (PLEM) (Liu N, et al., Advances in Genetics, 60: 325-405, 2008). Statistical configuration of haplotypes based on unphased genotype data usually gives a large number of uncertain haplotypes, which significantly reduces the power in genetic applications. In addition, it is still controversial as to whether the configured haplotypes should be treated as objective observations of genotypes and phenotypes in these studies. While genotypes from family members can often help to determine the haplotypes, haplotype inference from family data is often limited by uninformative or missing data. Moreover, late-age onset for most of the common human diseases can preclude collection of DNA samples from previous generations. Therefore, these methods are not suitable for the molecular diagnosis in personalized medicine in the future.

In parallel, some researchers developed experimental methods to extract the phase information in the genomic DNA samples before genotyping. These methods are all based on the physical separation of two homologous genomic DNAs before genotyping. The challenge is how to separate two almost identical copies of chromosomes in diploid cells. Several strategies/technologies have been developed for separating diploid samples into their haploid components, such as 1) Long-range allele-specific genomic PCR (Michalatos-Beloin S, et al., Nucleic Acids Res 24: 4841-4843, 1996; and Yu C E, et al., Genomics 84: 600-612, 2004); 2) Haplotype-Specific Extraction (HSE) (Nagy M, et al., Tissue Antigens 69: 176-180, 2007); 3) Generation of somatic haploid cells, such as GMP conversion (Douglas J A, et al., Nat Genet 28: 361-364, 2001); 4) Polony (Mitra et al., Proc Natl Acad Sci USA 100: 5926-5931, 2003; Zhang K, et al., Nat Genet 38:382-387, 2006); 5) Clone-based systematic haplotype (CSH) (Burgtorf C, et al., Genome Res 13: 2717-2724, 2003); 6) single molecule dilution (SMD) (Ding C, et al., Proc Natl Acad Sci USA 100: 7449-7453, 2003); and 7) Sperm typing.

Long-range Allele-Specific Genomic PCR uses specifically designed PCR primers to selectively amplify the target region from only one of the sister chromosomes. Selective amplification is achieved by designing a primer that will match/mismatch to one of the alleles at the 3'-end of the primer. Thus, the primer cannot amplify the unmatched chromosomal DNA template efficiently. Genotyping will be done subsequently on the amplification products. Because these PCR products are obtained from only one of the chromosomes, the alleles of different SNPs along these PCR products reveal the haplotype.

In this method, the maximal distance of the genetic markers in the haplotype is determined by the maximal length that PCR can reach and the chromosome integrity in DNA preparation. Therefore, the haplotype length is restricted by the PCR capacity, which is about 40 kb for long PCR. This method is often technically challenging and requires extensive optimization of PCR conditions for every primer pair to improve the amplification efficiency of long PCR. Different combinations of several primer pairs and buffers are usually recommended to optimize PCR condition. However, this method is not applicable to high throughput analysis of haplotypes.

Haplotype-Specific Extraction (HSE) uses specifically designed probes to selectively capture the fragments from only one of the sister chromosomes. Selective binding is achieved by designing a probe that specifically recognizes one allele of a SNP. If an individual is a heterozygote, when this probe is added into the denatured genomic DNA samples, the probe will seek and bind only to the genomic DNA fragments containing its target allele. Therefore, the probe-bound DNA fragments are captured by immobilized magnetic beads and the unbound DNA fragments with the other allele of this SNP will be washed away. Now the genomic DNA in diploid state is reduced to haploid state and ready for all subsequent analysis including genotyping/haplotype. Because distinct polymorphic differences always exist between two parental chromosomes, HSE can distinguish and separate the two parental copies for any chromosomal segments.

In this method, the maximal distance of the genetic markers in haplotype is determined by the chromosome integrity in DNA preparation and the DNA denaturation. This method can resolve haplotypes within a distance of <50 kb so far. If molecular haplotypes over extended distances are needed, multiplexed haploseparations have to be carried out.

GMP Conversion Technology is built upon constructions of cell hybrids from viable human cells (typically lymphocytes or fibroblasts) and a rodent cell line. Because these hybrid cells retain only a subset of human chromosomes, they can be either null, monosomic or disomic for each pair of human chromosomes. Those monosomic cells are haploid for the corresponding chromosomes and ready for subsequent genotyping assays for determination of haplotype.

In this technology, cells are electrofused and then propagated under a selective condition, for example, using the HPRT1/HAT (hypoxanthine, aminopterin, and thymidine)

system. After 2-4 weeks of growth, fused clones are harvested, and DNA is prepared for analysis. The monosomic clones can be identified by genotyping a few, highly polymorphic markers per chromosome, which minimally requires a single heterozygous genotype. Nonetheless, there are still some technical challenges on conversion-based haplotyping, including low DNA concentrations, preferential amplification, and insertions or deletions of chromosomal segments (Douglas J A et al., Nat Genet 28: 361-364, 2001).

It has been observed that whole chromosomes rather than chromosomal fragments are generally retained in the hybrid cells (Supra Douglas 2001). Therefore, this method does not have any restrictions on the distance of SNPs in a haplotype. The application of GMP Conversion Technology is restricted to a very limited number of subjects and chromosomal regions because of the inefficiencies and variations in fusion and selection conditions. Numerous cell lines are required for each individual. Conversion-based haplotyping is still very time-consuming and very costly.

Polony Technology uses a polyacrylamide gel to work on an in situ single molecule of chromosomal DNA. In this technology, genomic DNA from an individual is first diluted to a very low concentration, and then mixed with acrylamide and spread onto a glass microscope slide to form a thin DNA-containing polyacrylamide gel. Because the DNA concentration is so low, the DNA molecules are well separated from each other. An in-gel PCR is then performed directly on this gel, with 2 pairs of PCR primers to amplify two loci of the SNPs of interest from a single DNA molecule. Because the acrylamide matrix restricts the diffusion of linear DNA molecules, PCR products accumulate around their amplification template forming two overlapping PCR colonies (polony). The genotypes of these two SNPs are determined in situ by single-base extension (SBE) assay separately for these two SNPs and the gels are read by a laser scanner. After overlaying the two SBE images, the alleles observed on the same spot indicate the allele combination (haplotype) of these two SNPs of this patient sample.

The maximal haplotype length of Polony is determined by the DNA fragmentation or degradation before, during and after the acrylamide polymerization. It is reported that this method has measured the haplotype as long as 45 kb so far (Mitra, et al., PNAS USA 100: 5926-5931, 2003; Zhang K, et al., Nat Genet 38:382-387, 2006).

There are several inherent caveats in the Polony method. One major limitation of Polony haplotyping is that it is not efficient for scaling up the number of SNPs. But it is often desirable to haplotype a large number (100-10,000) of SNPs along a chromosome. Second, the DNA molecules may overlap in the gel. Therefore, the DNA concentration and plating condition is critical. Third, the PCR coamplification efficiency is low (4-15% for samples from buccal swabs, 15-34% for samples from the other collection methods). The coamplification efficiency is related to the presence of ungelled acrylamide in the Polony gel during thermal cycling and DNA fragmentation or degradation. Technical optimization (such as degas and polymerization condition) may be required. Lastly, this technology requires metaphase cells.

Clone-based Systematic Haplotyping (CSH) uses fosmid/cosmid cloning to isolate a single copy from diploid chromosomes. Because each vector molecule can hold only one insert molecule, each colony derived from successful vector-insert ligation will hold only a haploid chromosomal segment. By screening the colony library, the clones that contain the target chromosomal segments will be obtained for subsequent haplotyping analysis. Because the vector cannot successfully accept inserts with a very large size beyond their maximal cloning capacities, CSH can separate a haploid fragment of ~50 kilobases. In addition, this method is very time-consuming and costly.

Single Molecule Dilution (SMD) is built upon the idea that a single molecule is certainly a haploid fragment because diploid chromosomes are a pair of copies and require two DNA molecules to constitute a diploid. To obtain a single molecule in each reaction tube, genomic DNA samples are diluted to an extremely low concentration. We have known that each diploid genome of human is ~6.7 pg, so if a tube contains only ~3.3 pg of genomic DNA, it must have single molecules for some chromosomal regions because the DNA amount is not sufficient for every chromosomal region to have two copies in that tube. This very low DNA concentration is achieved by serial dilutions. After serial dilution, for any given chromosomal segment, each tube may contain no DNA, one molecule of DNA for that region, or two molecules of DNA for that region. The tiny amount of DNA samples in these tubes is then amplified and genotyped; allele drop-out at previously identified heterozygous SNP loci of this individual is used to screening out the "single-molecule" tubes for further experiments. The caveat of this method is that it relies on statistical isolation of single DNA molecules, so there is no experimental guarantee for its success.

In this method, due to frequent shearing in serial dilutions, genomic DNA is broken down. The maximal distance is so far reported to be 24 kb in haplotyping distance (Ding C, et al., PNAS USA 100: 7449-7453, 2003).

Sperm Typing is built upon the fact that a sperm is a product of meiosis and only contains a haploid genome. Despite sperm being haploid, sperm haplotypes are not simply equal to the donor's haplotype. The sperm haploid genome is not any one of parental chromosomes of this individual. However, by genotyping several sperms from one individual and then analyzing the haplotype data from these sperms, the haplotypes of this individual can be inferred. Therefore, sperm typing is different from the above molecular haplotyping methods because it is not a direct haplotyping.

Different sperms have gone through different crossing over events in meiotic recombination, so sperms from the same individual will have different haplotypes. In crossing over, two chromatids exchange their distal arms of chromosomes; usually this distal end of the chromosomes are exchanged only once in humans, sometimes twice or more times. Therefore, it is possible to infer the haplotypes of the original patient from a number of sperm under the assumption that only one crossing over event occurred in the studied sperms. However, since sperm typing is limited to male only, the procedure is tedious and costly, and the haplotypes are inferred results, not direct observations; sperm typing is not widely used for molecular haplotyping.

In summary, the currently available experimental methods for chromosome separation often cause the chromosome breakdown so they cannot obtain the long-range haplotypes. In addition, they are extremely time-consuming and labour-intensive, so they are not practically feasible in researcher laboratories and clinics. There still exists a need for a haplotyping method that can be performed quickly at low cost.

SUMMARY

A method for molecular haplotyping of a subject is disclosed. The method comprises: randomly selecting a set of chromosomes in each of a plurality of lyzed diploid cells of the subject, collecting the selected chromosomes from said plurality of cells into a plurality of sample tubes, wherein each sample tube contains chromosomes selected from one or more cells, genotyping genomic DNA in each sample tube, and determining haplotype of alleles based on allele nucleotide sequence information and corresponding nucleotide signal intensities from genotyping data.

In one embodiment, the step of determining haplotype of alleles includes the steps of: extracting allele nucleotide sequence information and corresponding nucleotide signal intensities from genotyping data, calculating the nucleotide signal intensity ratio of two alleles (allelic intensity ratio) for each heterozygous locus, and determining haplotype of the alleles.

In another embodiment, the step of calculating allelic intensity ratio includes the steps of: calculating relative ratio of nucleotides A, C, G, and T at homozygous loci, determining a k value for each nucleotide to adjust their signal intensities to the same level, adjusting nucleotide signal intensities at heterozygous loci using the k value, and calculating the allelic intensity ratio at the heterozygous locus.

In another embodiment, the determining step further comprises the steps of sorting the order of alleles at each locus by allelic intensity ratio, keeping the higher-intensity-allele on a first column and the lower-intensity-allele on a second column, determining whether there is breakpoint in each chromosome, if there is no breakpoint in a chromosome, forming one haplotype with alleles in the first column, and another haplotype with alleles in the second column, if there is a breakpoint in a chromosome, using results from other chromosome collection tubes to bridge over the breakpoint.

In a related embodiment, the cells are peripheral blood lymphocytes.

In another related embodiment, chromosomes from 2-10 randomly selected cells are collected into a sample tube and a total of 4-8 sample tubes are collected.

In another related embodiment, the genotyping step comprises amplifying genomic DNA.

Also disclosed is another method for molecular haplotyping of a subject. The method comprises: isolating one or more single diploid cells from the subject, lysing each isolated single diploid cell to generate one or more single cell lysate, dividing each single cell lysate into two equal aliquots, genotyping genomic DNA in each aliquot, creating a catalogue of genotyping data from all aliquots, and determining chromosome haplotype of the subject based on the catalogue.

In a related embodiment, the isolating step includes isolating 4-12 single diploid cells from the subject.

In another related embodiment, the isolating step includes isolating 6-10 single diploid cells from the subject.

In another related embodiment, the isolating step includes isolating 8 single diploid cells from the subject.

Also disclosed is another method for molecular haplotyping of a subject. The method comprises: isolating a single diploid cell from the subject, lysing and staining the isolated single diploid cell to display chromosomes, collecting a set of chromosomes from the single cell by laser microdissection, genotyping genomic DNA in the collected chromosomes, genotyping genomic DNA from one or more intact diploid cells of the same subject, determining haplotype of a chromosome in the collect set of chromosomes, wherein said chromosome is present in a haploid form in said collected set of chromosomes.

In a related embodiment, multiple single diploid cells are isolated and lysed. Multiple sets of chromosomes are collected; each set is collected from a different single cell of the same subject. The number of collected sets is large enough so that each chromosome in the genome of the subject is present in the haploid form at a probability greater than 99%.

In a related embodiment, the subject is an eukaryotic organism.

In a related embodiment, the eukaryotic organism is an animal or a plant.

In a further related embodiment, the animal is a mammal.

Another aspect of the present invention relates to a computer-readable medium having computer-executable instructions for performing the methods described above.

Another aspect of the present invention relates to an assay kit for HaploDissection. In one embodiment, the assay kit contains reagents for cell collection and cytogenetic staining, and reagents for genomic DNA amplification and genome genotyping. In another embodiment, the kit further includes a computer readable medium having computer-executable instructions for determining haplotype based on genotyping data.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

The file of this patent contains at least one drawing executed in color. Copies of this patent with color drawings will be provided by the Patent and Trademark Office upon request and payment of the necessary fee.

The practice of the embodiments described in further detail below will employ, unless otherwise indicated, conventional methods of genetics, genomics molecular biology, cell biology, diagnostics and bioinformatics within the skill of the art. Such techniques are explained fully in the literature. All publications, patents and patent applications cited herein, whether supra or infra, are hereby incorporated by reference in their entirety.

One aspect of the present invention relates to a method for molecular haplotyping of a subject. This method is referred to hereinafter as the "HaploDissection" method. As described in more detail below, the new method overcomes the bottleneck on the haplotype length, and has no limitations on SNP numbers or sample numbers. This invention meets the needs of accurate haplotypes in genetic studies, genomic studies and epigenomic studies, especially the genome-wide association studies (GWAS), long-cis-regulatory interactions for gene expression, and chromatin remodelling studies. Accurate haplotypes are required for interpretation and translation of these results into clinical practice.

Figure 1:
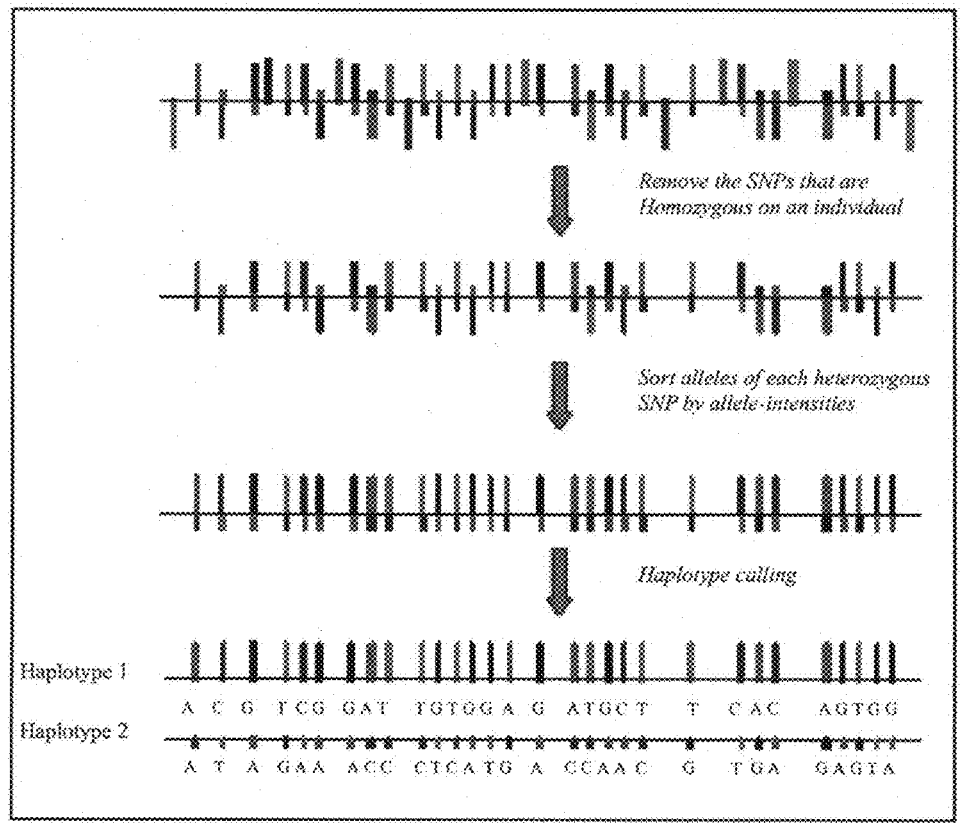
FIG. 1 is a schematic illustrating the general principle of an embodiment of the HaploDissection method by introducing imbalance into chromosome ratio.

One embodiment of the HaploDissection method is illustrated in FIG. 1. Briefly, the HaploDissection method maintains the phase information of DNA samples from a subject that are subjected to genotyping, but this maintenance is not based on the separation of two chromosome copies or isolation of a single copy. The method simply introduces an imbalance into the steady 1:1 ratio on the quantities of two parental chromosomes by harvesting a relatively small number of chromosomes into each sample tube. Thus, while the genotype/allele information is still reserved in the DNA samples and applicable to hi-throughput genotyping platforms, the phase information is recorded into the quantitative ratio between two alleles. These relative ratios of alleles are actually one of the outputs from all of those genotyping platforms, but they are usually ignored in the genotyping interpretation. The HaploDissection method will read the output information on both allele readings and allele intensity readings. The genotyping information and the phase information are then analyzed by a specially designed algorithm to determine the haplotype of the subject. In one embodiment, the genotyping information and the phase information are then analyzed by a special designed software called "HapReader."

Because the HaploDissection method protects the chromosome integrity while introducing the quantitative allele imbalance, the haplotypes obtained from this method will be at the entire chromosome range, or unlimited by distance.

Figure 2:
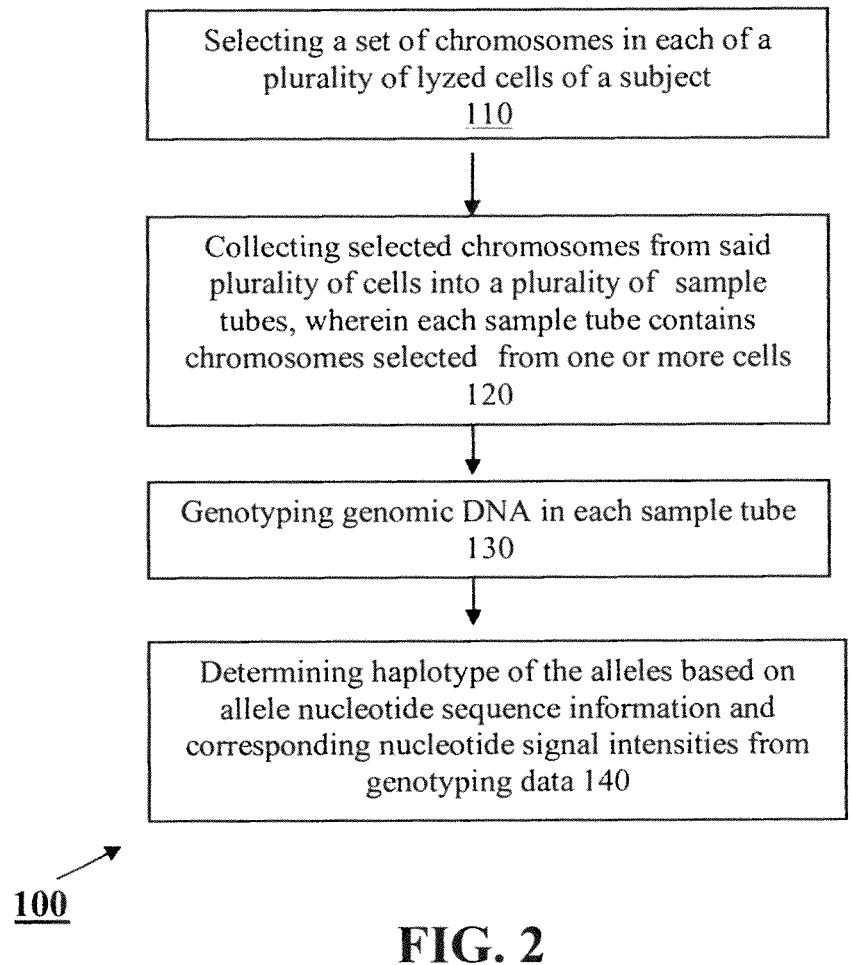
FIG. 2 is a flow chart showing an embodiment of the HaploDissection method.

An embodiment of the HaploDissection method is shown in FIG. 2. In this embodiment, the method 100 includes: selecting (110) a set of chromosomes in each of a plurality of lyzed cells of a subject; collecting (120) selected chromosomes from said plurality of cells into a plurality of sample tubes, wherein each sample tube contains chromosomes selected from one or more cells; genotyping (130) genomic DNA in each sample tube; and determining (140) haplotype of the alleles based on allele nucleotide sequence information and corresponding nucleotide signal intensities from genotyping data.

Figure 3:
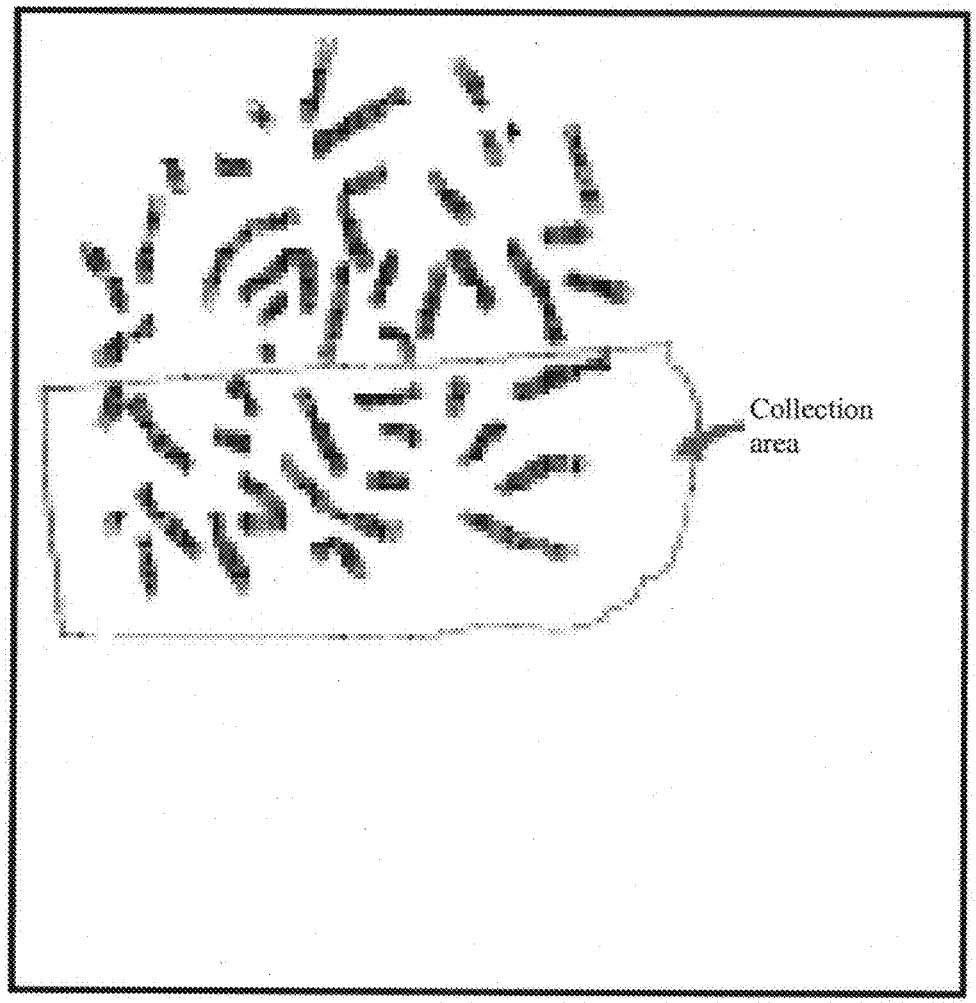
FIG. 3 is a picture showing chromosome collection using a Leica AS LMD computer-directed laser microdissection. Chromosomes in the collection area were collected for haplotyping.

The chromosomes may be selected from any type of cells. In one embodiment, the cells are peripheral blood lymphocytes isolated from a blood sample of the subject. Methods for isolating peripheral blood lymphocytes are well-known in the art. In one embodiment, the isolated peripheral blood lymphocytes are cultured in a growth medium until they start proliferation. Growth media capable of inducing proliferation are well known in the art. In one embodiment, the growth medium is RPMI1640 containing 15% FBS and 100 unit/ml Penicillin/Streptomycin. Mitogens such as phytohaemagglutinin (PHA) may be added to the culture medium to stimulate cell proliferation, and a mitotic inhibitor such as colcemid is added to arrest the cells in metaphase. The proliferating peripheral blood lymphocytes are then harvested, lyzed, and stained to display chromosomes using well-known cytogenetics procedures. A set of chromosomes, typically around half of the chromosomes in a lyzed cell, is randomly selected and collected for further analysis. FIG. 3 shows an example of selecting chromosomes from a single cell for collection using computer-directed laser microdissection. Chromosomes in the marked area were collected. As noted earlier, the chromosomes are randomly selected for collection.

Randomly selected chromosomes from randomly selected cells are collected into a plurality of sample tubes. Each tube contains chromosomes collected from a plurality of cells. In one embodiment, each tube contains chromosomes collected from 2-20, preferably 2-10, randomly selected cells. A total of 2-12, preferably 4-8, and sample tubes were collected for each subject. The selected chromosomes are collected using technologies that preserve the chromosome integrity. In one embodiment, the chromosomes are collected using computer-directed laser microdissection.

In the next step, genotyping is performed on collected chromosomes in each sample tube. In one embodiment, the collected DNA is amplified by PCR using methods for unbiased whole genome amplification (WGA). The amplified DNA is then subjected to whole genome genotyping. For each subject, 2-4 tubes of samples will be subjected to the genotyping to ensure high genome coverage and achieve duplications for accuracy. In one embodiment, a genomic DNA sample is included for whole genome genotyping.

The output dataset from genotyping is analyzed to determine the haplotype of the subject using a method that integrates the sequencing information with the phase information, which is reflected on the intensity of sequencing signals at each loci. Briefly, the allele nucleotide sequence information and corresponding nucleotide signal intensities are extracted from the genotyping data obtained from the collected chromosomes in each sample tube. The nucleotide signal intensity ratio of two alleles (allelic intensity ratio) for each locus of a chromosome is calculated and is used for and determining the haplotype of the alleles.

Figure 4:
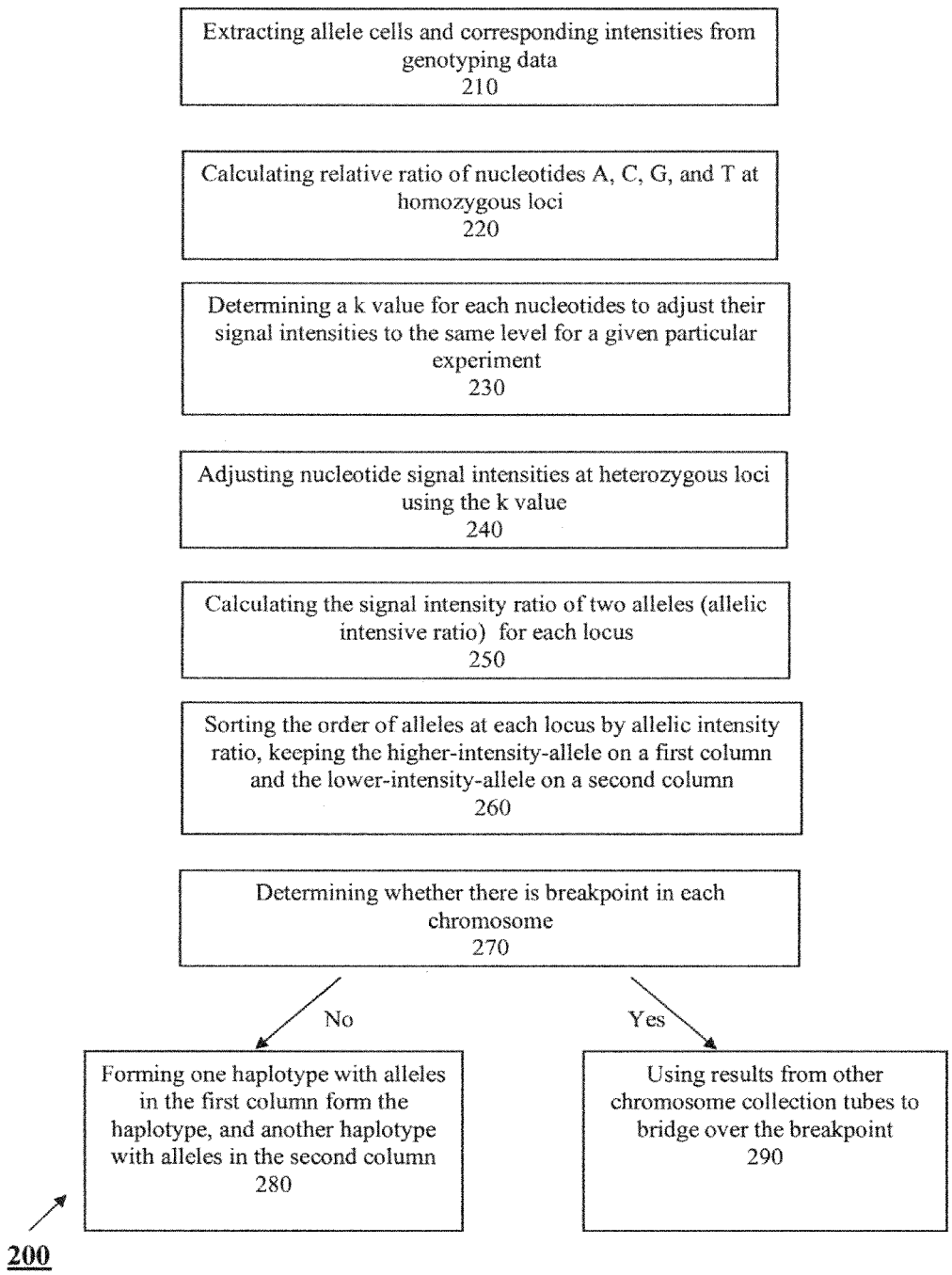
FIG. 4 is a flow chart showing an embodiment of a method for determining haplotype-based genotyping data.

FIG. 4 is a flow chart showing an embodiment of a method for determining allele haplotype based on the nucleotide sequence information and corresponding nucleotide signal intensities of the alleles. In this embodiment, the method 200 includes: extracting (210) allele nucleotide sequence information and corresponding signal intensities from genotyping data, calculating (220) relative ratio of nucleotides A, C, G, and T at homozygous loci, determining (230) a k value for each nucleotides to adjust their signal intensities to the same level for a given particular experiment, adjusting (240) nucleotide signal intensities at heterozygous loci using the k value; calculating (250) the signal intensity ratio of two alleles (allelic intensity ratio) for each locus; sorting (260) the order of alleles at each locus by allelic intensity ratio, keeping the higher-intensity-allele on a first column and the lower-intensity-allele on a second column, determining (270) whether there is breakpoint in each chromosome, if there is no breakpoint in a chromosome, forming (280) one haplotype with alleles in the first column forming the haplotype, and another haplotype with alleles in the second column, if there is a breakpoint in a chromosome, using (290) results from other chromosome collection tubes to bridge over the breakpoint.

In one embodiment, the analysis is performed using a "HapReader" software that is specifically developed for the HaploDissection technology. The software is described in more detail in the EXAMPLES.

Another embodiment of the HaploDissection method is based on the separation of haploid genome from a single cell lysate. In all of the current molecular haplotyping methods, the reduction from diploid to haploid is achieved from an uncertain and large number of chromosome copies. The method of the present invention is built upon the fact that each somatic cell has exactly two copies of each chromosome. This exact number provides a very simple way to separate the two chromosomes. Briefly, the method separates chromosomes on a single cell basis. This new starting point makes the separation much easier than previous inventions because there are only two copies of each chromosome at the starting point. In addition, the method overcomes a major drawback of the other methods—the short haplotype distance. Therefore, this new method opens the door to a simple and effective way to obtain long-distance haplotypes.

Figure 5:
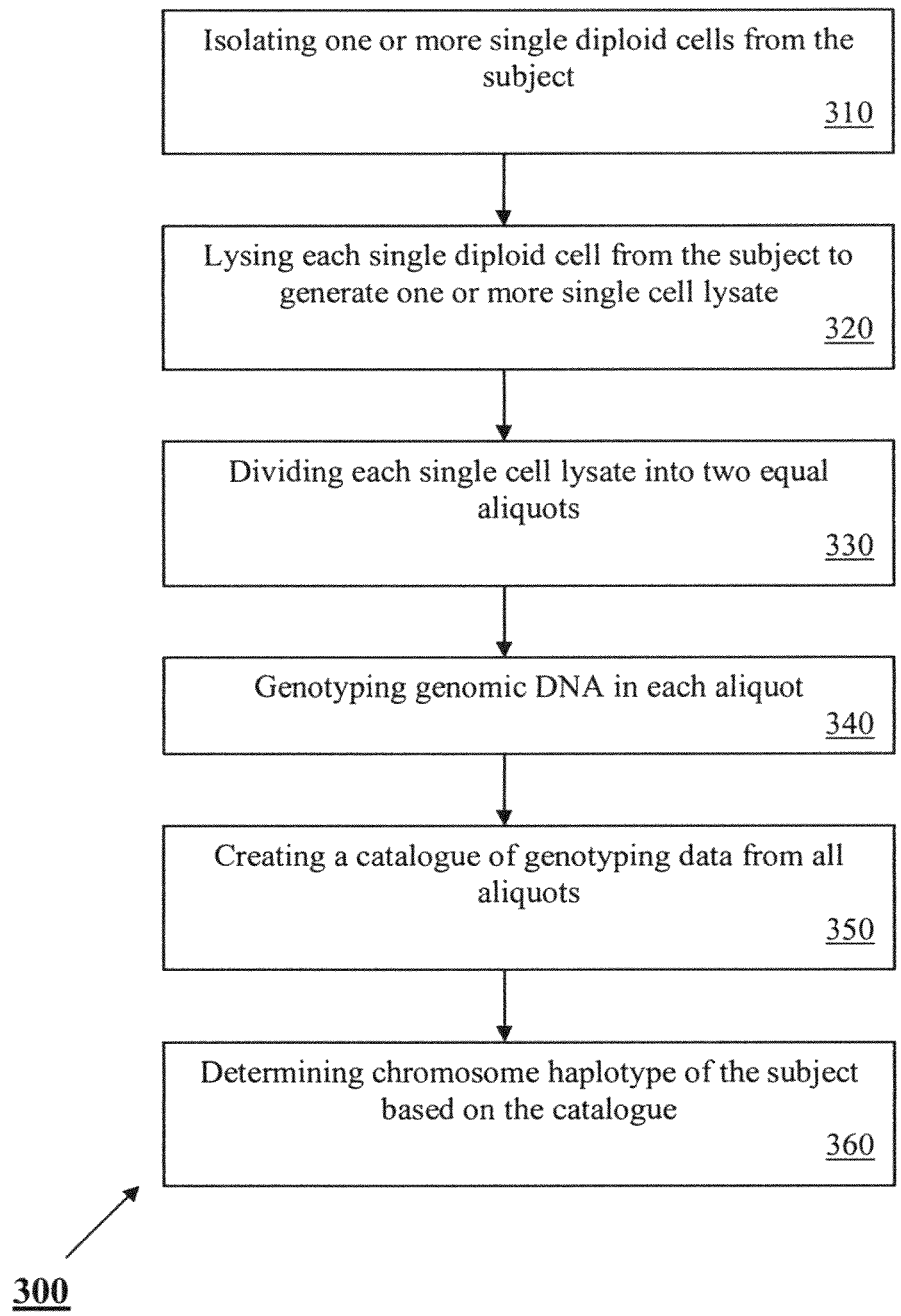
FIG. 5 is a flow chart showing another embodiment of the HaploDissection method using single cell lysate.

As shown in FIG. 5, the method 300 includes the steps of isolating (310) one or more single diploid cells from the subject; lysing (320) each single diploid cell from the subject to generate one or more single cell lysate; dividing (330) each single cell lysate into two equal aliquots; genotyping (340) genomic DNA in each aliquot; creating (350) a catalogue of genotyping data from all aliquots; and determining (360) chromosome haplotype of the subject based on the catalogue.

The diploid cells can be buccal cells, lymphocytes or any other cell types from the subject. In one embodiment, human buccal cells are collected from a subject. Buccal cells are the cells on the inner lining of the mouth or cheek. They are routinely shed and replaced by new cells. As the old cells die, they accumulate in the saliva in the mouth and can easily be collected by a simple procedure using mouthwash. Buccal cells can be easily collected by swabs, cytobrushes, mouthwash, and treated cards, such as FTA or IsoCode cards.

Next, single cells are isolated and kept in individual tubes. This can be done by any method that can isolate single cells while preserving genomic DNA in cells. Examples of such method include, but are not limited to, laser microdissection or flow cytometry.

In one embodiment, isolation of single cells is carried out using laser microdissection or any other methods such as cell sortings. Laser microdissection is a micromanipulation procedure that allows cutting off precisely the cells of interest from tissue samples or smears under direct microscopic visualization by a laser beam. The region of interest is marked on the computer monitor and then cut out by computer control. The single cell in the collection tube can be immediately checked by an inspection mode under the microscope to ensure the successful isolations.

The staining protocol used during cell isolation should not interfere with the subsequent DNA amplification and allele determination. Preferred staining methods do not include any fixation step and are not based on the use of aggressive chemical agents. In one embodiment, the cells are stained with Papanicolau. In another embodiment, the cells are stained with Hematoxylin and eosin (HE).

Single cells collected by microdissection are then subjected to cell lysis. Many techniques are available for cell disruption, including physical and detergent-based methods. The technique chosen for the disruption of cells must take into consideration the compatibility with the intended downstream applications—genotyping and haplotyping. Therefore, the cell lysis method should not attach the DNA molecules aggressively and break down the chromosomes into small pieces. Any genomic DNA preservative, effective, simple, and low-cost methods can be selected. The origin of the cells or tissues should also be considered with choosing cell lysis protocols.

Both physical lysis methods and detergent-based lysis methods may be used for cell disruption. Preferred cell lysis method includes hypotonic lysis and proteinase K lysis.

Next, the single cell lysate is divided equally into two tubes. To ensure that a haploid copy for any given chromosomes is collected, multiple single cell lysates and corresponding splits are collected. In one embodiment, 4-12 single cell lysates are collected. In other embodiment, 6-10 single cell lysates are collected. In yet other embodiment, 8 single cell lysates are collected.

Figure 6:
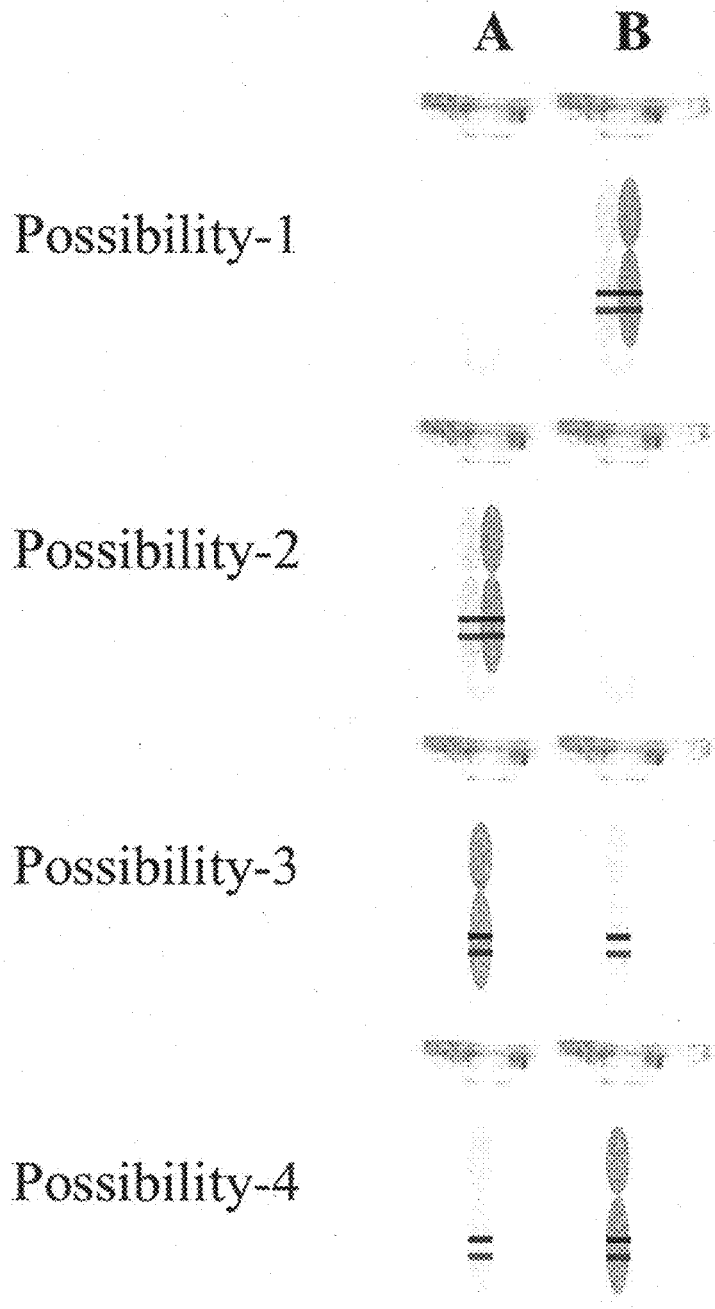
FIG. 6 is a diagram illustrating the principle of single cell haplotype split.

As shown in FIG. 6, a diploid cell contains two copies of each chromosome (one copy from father, one copy from mother). When a solution containing two copies of a chromosome is equally aliquoted into two tubes, the two copies may both go to tube 1 or tube 2, or they may each enter a different tube. The pattern of the chromosome presence in these two splitting tubes can be easily monitored. If one tube does not contain this chromosome, the other tube must contain both copies of the chromosome. If both tubes contain this chromosome, then they must contain one copy in each.

For one split operation, the probability of obtaining a haploid copy for any given chromosomes is:

$$\text{Success Probability} = \text{Failure Probability} = \frac{1}{4} + \frac{1}{4} = 0.50.$$

If n single cells are collected, and the splits describe above are performed n times (one for each single cell), then the probability that none of these tube pairs has a haploid copy for a given chromosome (all tubes are either diploid or aploid with regard to this given chromosome) is:

Failure Probability=½.sup.n.

Success Probability=1½.sup.n.

Therefore, if 8 single cells are collected (i.e., n=8) and split into 16 aliquots, the likelihood of obtaining a haploid copy of any particular chromosome in these splits is:

$1\frac{1}{2}^{8} = 0.9961.$

This means that there is a 99.61% chance that at least one of these 16 split tubes will contain a haploid copy of the target chromosome. Accordingly, if the sample size is 1000 human individuals, with 8 cells collected from each individual, in the first round of split operation, 996 individuals will successfully obtain a haploid copy of any chromosomes for molecular haplotyping.

After the split, one tube may contain a haploid copy for one chromosome; however, it may contain two copies of another chromosome. If one tube contains a haploid copy of chromosome A, two copies of chromosome B and no chromosome C, this tube can still be perfectly used for subsequent analysis (such as haplotype determination) on chromosome A. The presence of two copies of chromosome B and the absence of chromosome C will not interfere with the results on chromosome A.

There is an extremely rare case in which the haplotypes from one single somatic cell do not represent the haplotypes of the same individual. This rare case is mitotic crossover which occurs in somatic cells. It is known that mitotic crossover may occur in some asexually reproducing fungi and in human cancer cells. Therefore, it is necessary to take cautions and obtain multiple cells for haplotyping a subject with cancer. In fact, this case can be easily detected by the single cell split strategy.

Specifically, if a cell from an individual contains more than two copies of a certain chromosome, the presence of that chromosome in both split tubes will not be an indication of haploid chromosome in each tube. For example, if there are 3 copies of a chromosome, when both tubes contain this chromosome, one tube will have one copy, the other tube will have two copies. The tube with two copies will show heterozygous genotypes at some polymorphic sites. Therefore, our method may detect the copy number polymorphisms.

The genomic DNA in each tube is then amplified for genotyping. Any methods of unbiased whole genome amplification (WGA) may be employed. Unlike polymerase chain reaction (PCR), which aims to amplify a specific sequence, WGA aims to amplify the entire genome without preference. Comprehensive WGA requires faithful replication of 3 billion bases without the loss or distortion of any particular loci or alleles.

Examples of such methods include, but are not limited to, multiple displacement amplification (MDA, GE Healthcare GenomiPhi and Qiagen Repli-g), primer extension preamplification (PEP), improved primer extension preamplification (iPEP), degenerate-oligonucleotide-primed PCR (DOP, Sigma GenomePlex). The current WGA methods in the market are different on (i) amplification power and yield; (ii) fidelity; (iii) amplification product length; (iv) scalability and (v) the ability to amplify small amounts of starting material, including single cells. For example, Repli-g and GenomiPhi yield products around 10 kb in size, whereas the Sigma GenomePlex yields products around several hundred base pairs. Because the distance that the molecular haplotyping method of the present invention can resolve does not rely on the length of amplification product, the length feature of WGA method is not a critical feature for the present invention. Instead, the amplification power and potential allele bias and locus bias are critical to the present invention.

The feasibility of amplifying from haploid chromosomes has been previously well-demonstrated by the genetic research using human sperms. The ability to genotype single sperm was first reported in 1988 (Li H H, et al., Nature 335: 414-417, 1988). Now genotyping on the DNA samples from single sperm cells (haploid) has been widely used by forensic scientists (Di Martino D, et al., Forensic Sci Int 146 Suppl: S151-153, 2004). It has been shown that up to 10.4 pg of DNA can be amplified by TaqGold DNA polymerase for a reliable STR (short tandem repeats, a type of genetic polymorphisms in parallel to SNP) profile. In addition to single sperm cells, amplification of single lymphocytes (diploid) or single blastomeres (diploid) using the WGA-multiple displacement amplification (MDA) method has been successfully carried out.

A common concern of WGA is the allelic drop-outs at heterozygous loci, which is consequence of a biased uneven amplification among the two alleles at one polymorphic locus. The allele drop-out will make a heterozygous individual to display as a homozygous individual in genotyping. Accordingly, when a homozygous genotype was observed, it is still theoretically possible that this is false-homozygous genotype; it may come from allele drop-out in WGA. When using the cell-split method for molecular haplotyping, because there is a single copy of haploid, if there is no locus bias at a particular locus, the allele reading in the subsequent genotyping assays will represent the allele on that corresponding haplotype. Therefore, there will be no concern necessary to distinguish allelic dropout and true homozygotes.

As discussed above, if 16 split tubes from 8 single cells are collected from one individual, there is a 99.6% that some tubes contain a haploid copy of any given chromosome. Other tubes may contain diploid copies or no copy (aploid) of the same chromosome. Each tube may contain haploid copies of certain chromosomes, diploid copies of other chromosome(s), and no copy of yet other chromosome(s). Therefore, it is necessary to create a catalogue for each tube about its content for subsequent analysis, including haplotype determination.

The cataloguing can be done by any methods that can detect the DNA existence. For example, PCR can be used to detect the existence of DNA fragments. If the PCR is designed to cover a sufficient number of regions that representative all of the chromosomes of genome, then it can be used to create a genome wide catalogue. PCR can be also designed to cover only the target genome region of a research project. Besides, whole genome tiling array can be also used to create this catalogue, but in a more systematic and high-throughput pattern.

If both tubes of a split pair contain chromosome A, then both tubes have a haploid copy of chromosome A for haplotype determination. The tubes with a haploid copy of any particular chromosomes will be selected based on this catalogue for subsequent analysis. The samples from this procedure can be used as regular DNA samples and directly subjected to various high-throughput genotyping assays. In haplotype determination, the genotypes from haploid samples will be compared with the diploid samples from the same individual as quality control. Any false-haploid tubes will be easily detected by this comparison.

Another embodiment of the HaploDissection method allows for determination of haplotype of certain chromosomes from a single cell. The method comprises: isolating a single diploid cell from the subject, lysing and staining the isolated single diploid cell to display chromosomes, collecting a set of chromosomes from the single cell by laser microdissection, genotyping genomic DNA in the collected chromosomes, genotyping genomic DNA from another intact single cell from the same subject, determining haplotype of a chromosome in the collect set of chromosomes, wherein said chromosome is present in the haploid form in said collected set of chromosomes.

Figure 7:
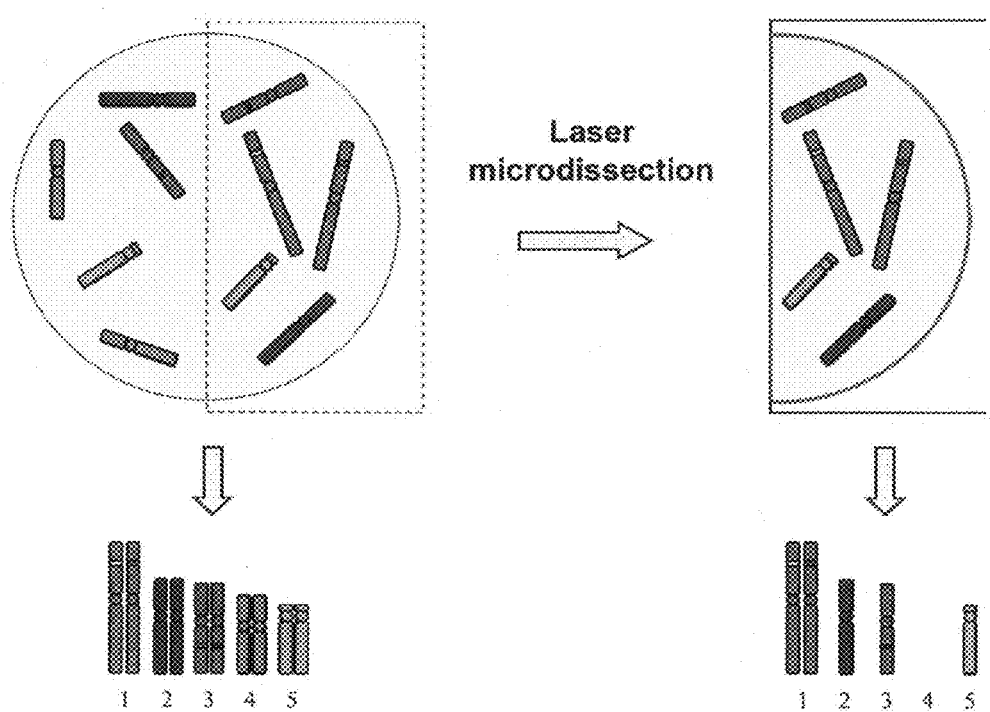
FIG. 7 is a diagram illustrating the principle of haplotyping with a HaploDissection method using single cell dissection.

As shown in FIG. 7, when a cell is cut along the dotted line and the right half of the cell is collected, the collected chromosomes include only a single copy of chromosomes 2, 3, and 5 (haploid) two copies of chromosome 1 (diploid) and no copy of chromosome 4 (aploid). Thus, the genotype calls from conventional genotyping platforms with this half cell will directly return the haplotypes for chromosomes 2, 3, and 5, whereas it will be still diploid genotypes for chromosome 1, and no genotype calls for chromosome 4.

As discussed earlier, for each given chromosome, there is a 50% chance that a haploid copy is collected if the collected a set of chromosomes contain about half of the total number of chromosomes in the single diploid cell. The probability increases significantly when multiple sets of chromosomes are collected from multiple single cells. For example, there is a greater than 99.6% chance that a haploid copy of a given chromosome is collected if 8 sets of chromosomes are collected from 8 single cells and each collected set of chromosomes contain about half of the total number of chromosomes in the single cell. Therefore, the haplotyping of the complete set of chromosomes from a subject may be achieved with high probability (greater than 99.6%) using 8 half cells.

Accordingly, in a related embodiment, multiple single diploid cells are isolated and lysed. Multiple sets of chromosomes are collected; each set is collected from a different single cell. The number of collected sets is large enough so that each chromosome in the genome of the subject is present in the haploid form at a probability greater than 99%.

The HaploDissection method described above applies to any eukaryotic organism. In certain embodiments, the subject is an animal or a plant. In other embodiments, the subject is a mammal. In yet other embodiments, the subject is a human.

Another aspect of the present invention relates to a computer-readable medium having computer-executable instructions for performing the methods of the present invention.

Another aspect of the present invention relates to an assay kit for HaploDissection. In one embodiment, the assay kit contains reagents for cell collection, cell lysis and, optionally, cytogenetic staining, as well as reagents for genomic DNA amplification and genome genotyping. In another embodiment, the kit further includes a computer readable medium having computer-executable instructions for determining haplotype based on genotyping data. In another embodiment, the kit further includes an instrument specifically designed for collecting a set of chromosomes from single or a few cells for haplotype reading and chromosome biology examinations.

In one embodiment, the HaploDissection methods are used in prenatal diagnostics to detect the important genotype defects of the fetus. It has been known that some fetus cells are circulating in the maternal peripheral blood. Therefore, the fetus cells can be collected from the pregnant maternal blood. These cells can be subjected to the haplotype analysis using the procedure described above. Because it is usually the haplotypes (the combination of alleles of different genotypes) that cause the diseases, the prenatal diagnosis by haplotype determination will be more accurate than genotype determination. The single cell nature of the present invention provides the feasibility of haplotype determination with fetus cells in the mother's blood.

In another embodiment, the HaploDissection methods are used in personalized medicine. Personalized medicine is the practice that doctors customize treatment based on a person's specific genetic variations. For instance, two people who take the same anti-hypertension medication may have very different responses. One may have severe, even life-threatening side effects, while the other experiences few if any side effects and seems to sail through the treatment. The reason why the two people have such drastically different reactions to the same medication resides in their genes. People inherit variations in their genes, and even slight variations can have a profound effect on which subtypes of the same disease the person has and how the person responds to certain medications.

In a personalized medicine, the current process in a clinic began to change. Before a patient takes a single dose of medication, the patient may have a blood test done to determine genetic variations. The test may show that patient's variation which is likely to have an adverse effect on the particular medication. The doctors can determine the drug prescriptions and doses to match the patient's genetics. Therefore, the unique genetic profile can help doctors to personalize treatments of patients, improve the drug development, and reduce healthcare costs.

It has been widely accepted now that multi-SNP haplotypes are more accurate to represent a person's genotype than single-SNP genotype. However, there is no simple, cheap and high-throughput experimental method to directly read the haplotypes. The statistical haplotype configuration causes many ambiguities. This technical bottleneck is not only limiting the efforts to discover the genetic basis underlying the common diseases, it is also limiting the application of genetic tests in clinical practice. The HaploDissection methods may solve this technical bottleneck.

For example, before a patient takes any medication, a few cells will be collected from his mouth and haplotypes on those disease mutations will be determined by using the present methods. Doctors will prescribe a drug with a certain dose to match a patient's unique genetic profile to personalize the treatment.

In yet another embodiment, the HaploDissection methods are used in forensic testing. True haplotyping provides a greater precision than single SNP genotyping in forensic studies, in any case of sexual assault or other crimes, as well as paternity testing. In many cases of forensic tests, the available amount of a specimen is usually quite limited. Because of the single cell nature of our invention and true haplotype result out of this technology, the HaploDissection method will increase both sensitivity and precision.

The present invention is further illustrated by the following examples, which should not be construed as limiting. The contents of all references, patents and published patent applications cited throughout this application, as well as the Figures and Tables, are incorporated herein by reference.

Example 1

Preparation of Cells

I. Sample Collection
Collect blood from human individuals and isolate the lymphocytes.
II. Cell Culture
Culture the lymphocytes in RPMI1640 medium containing 15% FBS and 100 unit/ml Penicillin/Streptomycin.
III. Cell Lysis
1. At the proliferation stage, add phytohaemagglutinin to the cell culture.
2. Harvest cells 48 hours after phytohaemagglutinin (PHA) treatment.
3. Add Ethidium Bromide (16.7 ug/ml) and Act-D (6.7 ug/ml) into cells.
4. Incubate at 37.degree. C. for 0.5 hour. After 0.5 hour, add colcemid (0.083 ug/ml) into cells and incubate at 37.degree. C. for 1 hour.
5. Centrifuge at 1000 rpm for 10 min.
6. Aspirate all but 0.3 ml supernatant, gently resuspended cell pellet. Add pre-warmed 0.075 mol/L KCl vortex gently to make sure KCl is mixed well with the pellet.
7. Leave at 37.degree. C. for 20 min and room temperature for additional 5 min. Centrifuge at 1000 rpm for 10 min. And remove the supernatant.
8. Add cold fixative (methanol: acetic acid, 3:1), gently mix by inverting tubes.
9. After fixed and centrifuged for three times, cells were dropped on slide and geimesa staining for 20 minutes.
10. Air dry slide for 20 min in hood.
IV. Chromosome Isolation
1. Turn on the laser, microscope (Leica, ASLMD) and computer. Put PCR tubes in collectors on holders.
2. Put slide on supporter.
3. Go to the computer screen. Click on LEICA ADMINISTRATOR to open program.
4. Set objective 10× to find cells and then switch to 40×.
5. Collect chromosomes: cut and pick up no more than 30 chromosomes at random from each cell. Collect 4-8 samples. Each sample contains chromosomes from about 7~11 cells.
6. Exit LEICA ADMINISTRATOR program.
7. Turn off the computer, microscope and laser by order.

Example 2

Whole-Genome DNA Amplifications

Single Cell Lysis and Fragmentation
1. Isolate a single cell into a PCR-ready vessel using laser capture micro-dissection, cell sorting, or other method. If sorted, the buffer should be of low ionic strength, such as Tris EDTA (TE) buffer, and in the minimal sort volume.
2. Add a sufficient volume of water to the single cell sample for a final volume of 9 mL.
3. Prepare a working Lysis and Fragmentation Buffer Solution by adding 2 mL of Proteinase K Solution into 32 mL of the 10 Single Cell Lysis & Fragmentation Buffer and vortex thoroughly.
4. Add 1 mL of the freshly prepared Proteinase K Solution-10' Single Cell Lysis & Fragmentation Buffer to the single cell sample and mix thoroughly.
5. Incubate DNA mix at 50.degree. C. for 1 hour, then heat to 99.degree. C. for EXACTLY four minutes. Note that the incubation is very time-sensitive and any deviation may alter results. Cool on ice. Spin down sample prior to proceeding to Library Preparation.

Library Preparation

6. Add 2 mL of 1 Single Cell Library Preparation Buffer to each sample.

7. Add 1 mL of Library Stabilization Solution.

8. Mix thoroughly and place in thermal cycler at 95° C. for 2 minutes.

9. Cool the sample on ice, consolidate the sample by centrifugation, and replace on ice.

10. Add 1 mL of Library Preparation Enzyme, mix thoroughly, and centrifuge briefly.

11. Place sample in a thermal cycler and incubate as follows:

16° C. for 20 minutes; 24° C. for 20 minutes; 37° C. for 20 minutes; 75° C. for 5 minutes; and 4° C. hold.

12. Remove samples from thermal cycler and centrifuge briefly. Samples may be amplified immediately or stored at −20° C. for three days.

Amplification

13. Add the following reagents to the entire 14 Ml reaction:

7.5 mL of 10' Amplification Master Mix; 48.5 mL of Nuclease-Free Water; and 5.0 mL of WGA DNA polymerase.

14. Mix thoroughly, centrifuge briefly, and begin thermocycling. The following profile has been optimized for a PE 9700 or equivalent thermal cycler:

Initial Denaturation at 95° C. for 3 minutes.

Perform 35 cycles as follows:

Denature at 94° C. for 30 seconds; anneal/extend at 65° C. for 5 minutes; and hold at 4° C.

After cycling is complete, maintain the reactions at 4° C. or store at −20° C. until ready for analysis or purification. The stability of WGA DNA is equivalent to genomic.

DNA stored under the same conditions.

Example 3

Whole Genome Genotyping

The amplified DNA will be subjected to Illumina high-throughput whole genome genotyping such as Hap3000K and others. For each person, 2-4 tubes of samples will be subjected to the genotyping to ensure high genome coverage and achieve duplications for accuracy. A genomic DNA sample will be included for whole genome genotyping. This step can be done also by using other high-throughput genotyping platforms.

Example 4

Haplotype Determination

Whole-genome genotyping data was obtained from Illumina HumanCNV370-Duo BeadChip. This BeadChip content covers over 370,000 markers using the Infinium®. Assay. After scanning, all the data uploaded into BeadStudio and analyzed using the BeadStudio Genotyping Module, version 3. After stringent filtering with removal of SNPs with missing genotype, the remaining SNPs were available for analysis. The values of theta, R, X and Y in the Illumina genotyping output are used to determine the relative ratio of two alleles of each SNP. Haplotypes are constructed by the allele ratio along the chromosomes.

The haplotype construction is done by using the software "HapReader," which is specifically developed for this technology. The essential procedure and algorithm is below:

1) The analysis will be done at an individual level, person by person. There will be no combination of datasheet from different individuals.

2) Each person will have 3-5 genotyping datasheets, one if from the genomic DNA, and the others are from the chromosome collection tubes. Extract the allele calls and their corresponding signal intensities from each Illumia output data sheet.

Based on the datasheet from the genomic DNA sample, select the homozygous loci for this person. Calculate the relative ratio of the averages of the A, C, G, and T at these loci. Determine a k value for A, C, G, T to adjust their intensities to the same level for a given particular experiment.

4) Using these k values, adjust the heterozygous loci.

5) For each locus, calculate the ratio of the two alleles.

6) For each locus, sort the order of those two alleles by their allelic intensity ratio. Sort all loci by the same way, and keep the higher-intensity-allele on column-A and the lower-intensity-allele on column-B.

7) Examine and compare the ratio values along the chromosome to determine if there is breakpoint in each chromosome.

8) If not at step 7), the alleles in column-A faun haplotype, and the alleles on column-B will form another haplotype for this person. If yes at step 7), use the results from other chromosome collection tubes to bridge over this breakpoint.

One aspect of the present invention lies under this step. Collect chromosomes into PCR tubes by microdissection using a Leica ASLMD Laser microdissection system. In this step, not all chromosomes are collected from one cell; instead, only part (around half) of the chromosomes is collected from any single lyzed cell (FIG. 2). The selection of chromosomes on any lyzed cells is random. This random collection is respected from 5-11 randomly-selected cells. All of the chromosomes from these 5~11 microdissections are collected into one tube. 4-8 tubes are collected for each person. In this step, the chromosome integrity is preserved by selecting the laser cutting line on the computer, so chromosome integrity is ensured.

Amplify the collect DNA sample in each PCR tube by using the Sigma GenomePlex WGA-4 kit for 20-24 cycles. In fact, this step can be done with any methods of unbiased whole genome amplification (WGA). These methods include, but are not limited to, multiple displacement amplification (MDA, GE Healthcase GenomiPhi and Qiagen Repli-g), primer extension preamplification (PEP), improved primer extension preamplification (iPEP), and degenerate-oligonucleotide-primed PCR (DOP, Sigma GenomePlex). Repli-g and GenomiPhi yield products around 10 kb in size, whereas the Sigma GenomePlex yields products around several hundred base pairs.

Example 5

Determination of Haplotype Using Single Cell Lysate Method

A Leica AS LDM Laser Microdissection system (Leica Microsystems, Germany) is used to isolate single cells from fresh cytobrush-swab buccal cells from human individuals. Briefly, buccal cells are smeared on a foiled slide (a rectangular UV-sliceable piece of foil fixed at the margins to a normal microscope slide), air-dried for 5 min and then stained very briefly. The section is reviewed under microscope, single cells are selected and cut-off from the foiled slide with the Laser Microdissection system. Single cells are collected into tubes with 10-ul of cell lysis buffer in each tube. The single cell lysate in each tube is then divided equally into two tubes. The genomic DNA in each tube is amplified WGA for genotyping. A genome wide catalogue is created using the genotyping data. Haplotype determination is carried out using the catalogue.

Example 6

Determination of Haplotype Using Single Cell Dissection Method

Chromosome Microdissection:

Lymphocytes were cultured in RPMI1640 medium containing 15% FBS and 100 unit/ml Penicillin/Streptomycin. Cells were stimulated by phytohaemagglutinin (PHA) for 48 hours, followed by addition of Ethidium Bromide (16.7 ug/ml) and actinomycin D (6.7 ug/ml) and incubation at 37° C. for 30 min. Colcemid (0.083 ug/ml) was added into cells and incubate at 37° C. for 1 hour. Cells were collected by centrifugation at 1,000 rpm for 10 min, resuspended, incubated in pre-warmed 0.075 mol/L KCl at 37° C. for 20 min, and then, at room temperature for 5 min. After fixation with cold fixative (methanol:acetic acid, 3:1), cells were dropped onto slide to break the nuclei followed by Giemsa staining for 20 min. Laser Microdissection Microscope (ASLMD, Leica, Germany) was used to collect half of the chromosomes of one cell.

Whole Genome Amplification (WGA):

The collected chromosomes were amplified by the Sigma GenomePlex WGA4 kit following the manufacturer's protocol. Briefly, the sample was incubated in the Lysis and Fragment Buffer at 50° C. for 1 hour, and then heated to 99° C. for 4 min. Then the Single Cell Library Preparation Buffer and Library Stabilization Solution was added into the sample followed by an incubation at 95° C. for 2 min. Library was prepared with the following cycles: 16° C. for 20 min, 24° C. for 20 min, 37° C. for 20 min, and 75° C. for 5 min. DNA was amplified by an initial denaturation at 95° C. for 3 min followed by 35 cycles of 94° C./30 sec and 65° C./5 min. Amplified DNA was purified by QIAquick PCR purification kit.

Genotyping:

The Illumina HumanCNV370-Quad BeadChip was used for genotyping. This BeadChip contains 370,000 markers including SNPs and copy number variation (CNV) markers. Three independent microdissected samples and one genomic samples extracted with a Qiagen kit were subjected to genotyping experiments. After scanning, the data was uploaded into the BeadStudio and analyzed using the BeadStudio Genotyping Module version 3. No-call threshold was set at default (0.15).

Data Analysis:

Unphased genotypes of GM1 0847 and his parents (GM and GM) were retrieved from the International HapMap Project database (Phase 2 Public Release #22, and Phase 3 Public Release #1, Phase 2+3 Release #27). The unphased genotypes of GM10847 were also retrieved from the Illumina database. Haplotypes of GM 10847 was computationally reconstructed with his parental genotypes by determining the parental origin of each allele following the Mendelian Law of Inheritance. In the data analysis, only those heterozygous loci of GM10847 were subjected to haplotype determination. The homozygous loci were removed because they do not have the haplotyping issue (phase-known). Allele calls with both allele intensities below 1,000 in the Illumina genotyping output were removed. Genome-wide RepeatMasker detection was retrieved from the UCSC Genome Browser (Human 2006 March Assembly). All data integration was performed with SAS9.1.

Figure 8:
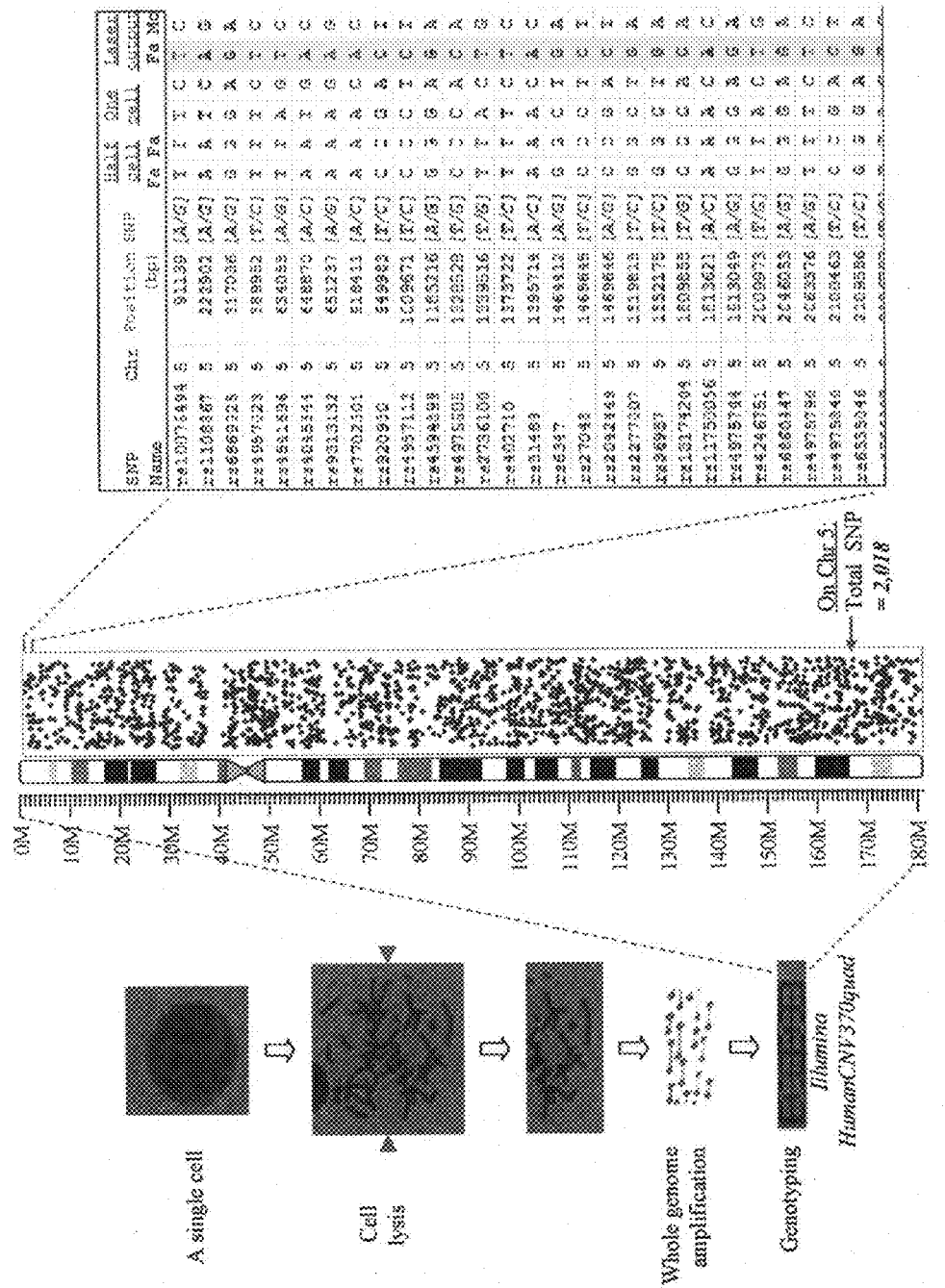
FIG. 8 is a flow diagram showing the steps of single cell dissecting method and some haplotyping results. Haplotypes are shown by their parental origins (Fa, father; Mo, mother).

The haplotyping method was tested with the individual GM 10847 recruited in the HapMap project (The International HapMap Consortium 2003) by three independent experiments. Following the procedures described above, we the genotype calls of microdissected samples were compared with genotype calls of genomic DNA as well as of data downloaded from the International HapMap Project database (Phase 2 Public Release #22). The monosomic, disomic and null states of each chromosome in each sample were indicated by whether the chromosome-wide heterozygous calls were converted to homozygous calls in the microdissection samples (FIG. 8). It was found that that sample 1 successfully haplotyped chromosomes 2, 4, 6, 15, 16, 17, 18, and 20; sample 2 haplotyped chromosomes 1 q, 3, 4, 5, 10, 16, 17, 18, 20 and 21; sample 3 haplotyped chromosomes 3, 7, 9, and 20. Totally 24,481 heterozygous loci were phased.

The accuracy of this method was determined by replications and comparison with haplotypes resolved from unphase genotypes (HapMap Phase2 Rel#22) using the trio structure under Mendelian Law of Inheritance (Hodge S E, et al., Nat Genet. 21(4):360-1; 1999). Among those 24,245 SNP loci that were successfully phased by our 7DDNA haplotyping method, 464 SNP loci were not covered by the HapMap Phase 2 genotype data, 4,744 SNPs do not have unambiguous haplotypes from the HapMap genotypes due to all-three-heterozygote, and 142 SNPs were not phased due to missing data in HapMap2. So we compared 18,895 SNP loci between our haplotypes and HapMap2 derived haplotypes. There were 18,625 SNPs (98.57%) that showed consistent allele phase as compared with haplotypes resolved by HapMap trio structure. Among those 270 discordant SNP loci, 45 SNP loci were due to the HapMap Phase 2 genotyping error as compared with phase 3 genotype calls, and 103 loci were on various repeats as detected by RepeatMasker. The other discordance may be potentially ascribed to whole genome amplification errors, genotyping errors, or un-annotated segmental duplications besides those identified by RepeatMasker. It was further determined the accuracy directly by 2,089 replications, among which 2,065 SNPs showed consistent result, none of them had inconsistent haplotype, and 24 SNP loci had diploid allele calls in one of the duplicates although the entire chromosome showed discordance (Table 1), with an estimate of 98.85% as the accuracy rate.

TABLE 1

An estimate of accuracy rate by data reproductivity.

| Chr | Total repeated SNPs | Consistent | Inconsistent | Accuracy % |
| --- | --- | --- | --- | --- |
| Chr3 | 517 | 516 | 1 | 99.81 |
| Chr4 | 565 | 554 | 11 | 98.05 |
| Chr16 | 189 | 186 | 3 | 98.41 |
| Chr17 | 217 | 215 | 2 | 99.08 |
| Chr18 | 212 | 208 | 4 | 98.11 |
| Chr20 | 389 | 386 | 3 | 99.23 |
| Total | 2,089 | 2,065 | 24 | 98.85 |

This haplotyping method does not have apparent limitations on the phasing distance, total SNP number, and marker types. The procedure is simple and inexpensive; it does not require a complicated optimization of experimental condition and the cost is close to conventional high throughput genotyping assays. In addition, there is no apparent barrier for this approach to be amendable to automation if chromosome microdissection is automated. The method may be further improved by using better WGA method for single-cell DNA, newer versions of high-throughput genotyping chips or deep sequencers, and more specific chromosome staining, such as chromosome painting of particular chromosomes.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The embodiments are intended to cover the components and steps in any sequence which is effective to meet the objectives there intended, unless the context specifically indicates the contrary.

What is claimed is:

1. An assay kit for high-throughput whole genome haplotyping of a subject, comprising:
(a) reagents for single cell collection and cytogenetic staining;
(b) reagents for single cell genomic DNA amplification and genome genotyping, and
(c) a non-transitory computer readable medium having computer-executable instructions facilitating a determination of a subject's haplotype,
wherein each single cell lysate comprises a partial set of the total chromosomes present in the single cell of the subject from which the lysate was derived,
wherein the computer-executable instructions are configured to:
(1) assemble an allelic genotype from nucleotide sequence information obtained from a subset of a subject's chromosomal DNA to produce a first set of genotyping data;
(2) assemble an allelic genotype from nucleotide sequence information obtained from the subject's total genomic DNA;
(3) determine a haplotype of alleles in said subject based on a comparison of the allelic genotypes in steps (1) and (2); and
(4) repeat steps (1) to (3) to determine the haplotypes of additional alleles.

2. The assay kit of claim 1, wherein steps (1) to (4) further comprise computer-executable instructions configured to:
(5) determine the nucleotide sequences and nucleotide signal intensities from the set of chromosomes by hybridization to single-nucleotide polymorphism (SNP) probes.

3. The assay kit of claim 1, wherein step (3) further comprises computer-executable instructions configured to:
(3a) assemble nucleotide sequence information and corresponding nucleotide signal intensities from the corresponding genotyping data; and
(3b) calculate the nucleotide signal intensity ratio of two alleles from each of a plurality of heterozygous loci.

4. The assay kit of claim 3, wherein step (3b) further comprises computer-executable instructions configured to:
(3bi) calculate relative ratios of nucleotides A, C, G, and T at homozygous loci;
(3bii) determine k values for each nucleotide to adjust their signal intensities to the same level;
(3biii) adjust nucleotide signal intensities at heterozygous loci using the k value; and
(3biv) calculate the allelic intensity ratio at each of said plurality of heterozygous loci.

5. The assay kit of claim 4, further comprising computer executable instructions configured to:
(6) sort the order of alleles at each locus by allelic intensity ratio;
(7) separate the higher-intensity-alleles in a first column and the lower-intensity-allele in a second column; and
(8) determine whether there is breakpoint in each chromosome,
wherein if there is no breakpoint in a chromosome, computer executable instructions in the non-transitory computer readable medium determine a first haplotype from the alleles in the first column and a second haplotype from the alleles in the second column, and
wherein if there is a breakpoint in a chromosome, computer executable instructions in the non-transitory computer readable medium utilize genotyping data of the same chromosome collected from a different cell to bridge over the breakpoint.

6. The assay kit of claim 1, further comprising an instrument for collecting a set of chromosomes from a single cell.

7. An assay kit for molecular haplotyping of a subject, comprising:
   (a) reagents for single cell collection and cytogenetic staining;
   (b) reagents for single cell genomic DNA amplification and genome genotyping, and
   (c) a non-transitory computer readable medium having computer-executable instructions facilitating a determination of a subject's haplotype based on a comparative analysis of nucleotide sequence information obtained from a plurality of single cell lysates obtained from a subject,
   wherein the computer-executable instructions are configured to:
   (1) separately determine allelic genotypes from genomic DNA present in each of two aliquots split from a single cell lysate;
   (2) create a catalogue of allelic genotypes obtained from a plurality of single cell lysate aliquot pairs; and
   (3) determine a chromosomal haplotype of the subject from the plurality of single cell lysate aliquots present in the catalogue.

\* \* \* \* \*

SEQUENCE LISTING

<160> NUMBER OF SEQ ID NOS: 2

<210> SEQ ID NO 1
<211> LENGTH: 30
<212> TYPE: DNA
<213> ORGANISM: Homo sapiens

<400> SEQUENCE: 1
acgtcggatt gtggagatgc ttcacagtgg         30

<210> SEQ ID NO 2
<211> LENGTH: 30
<212> TYPE: DNA
<213> ORGANISM: Homo sapiens

<400> SEQUENCE: 2
atagaaaccc tcatgaccaa cgtgagagta         30